United States Patent [19]
Desjardins

[11] Patent Number: 4,963,252
[45] Date of Patent: Oct. 16, 1990

[54] DECANTER DEVICE

[76] Inventor: Gaétan Desjardins, 8170 Yves Prévost, Ville d'Anjou, Quebec, Canada

[21] Appl. No.: 458,449

[22] Filed: Dec. 28, 1989

[51] Int. Cl.$^5$ ............................................. B01D 21/24
[52] U.S. Cl. ............................... 210/172; 210/532.1; 210/540; 222/209
[58] Field of Search ...................... 210/172, 532.1, 540; 222/207, 209, 395, 642

[56] References Cited

U.S. PATENT DOCUMENTS 2,431,192  11/1949  Munson ............................... 222/209
4,818,706  4/1989  Starr .................................. 222/642 X

*Primary Examiner*—Frank Spear
*Attorney, Agent, or Firm*—ROBIC

[57] ABSTRACT

Disclosed is a decanter device for use to withdraw supernatant liquid from a reactor tank containing a mixture of liquids of different densities or a liquid mixed with solid particles to be separated. The device comprises a perforated pipe mounted inside the tank. The pipe has a plurality of inlets in the form of small orifices opening into the tank, and at least one outlet leading out of the tank. An inflatable membrane is mounted inside the pipe in such a manner as to extend over the small orifices and sealingly close the inlets of the pipe when it is inflated, and to extend away from the small orifices and away from the outlet to allow supernatant liquid to flow out of the tank through the pipe when the membrane is not inflated. A source of air or water under pressure is used for inflating the membrane whenever desired to sealingly close the inlets of the pipe and thus prevent liquid or solids to penetrate in the pipe during reaction within the reactor tank. This device is particularly useful for biological wastewater treatment reactors.

7 Claims, 4 Drawing Sheets

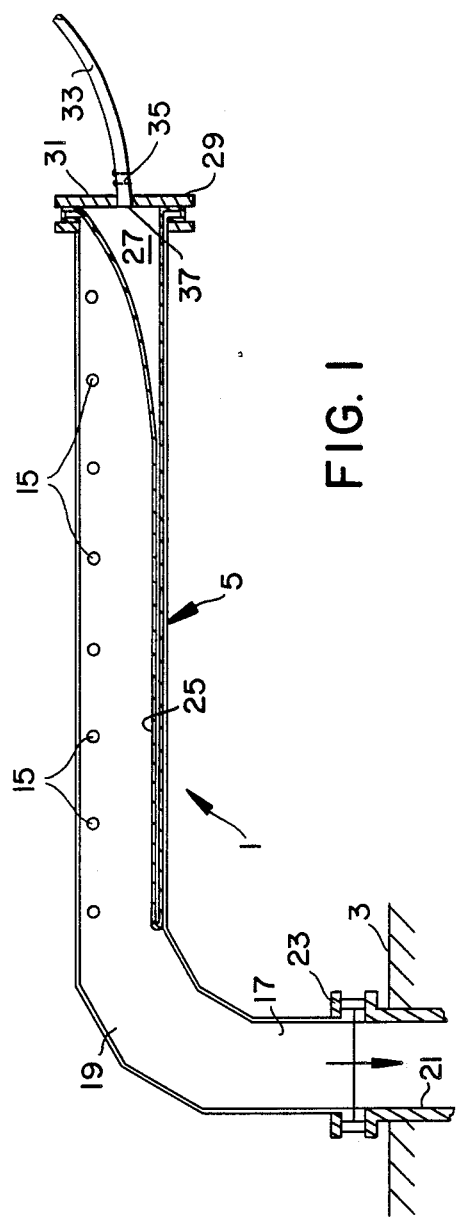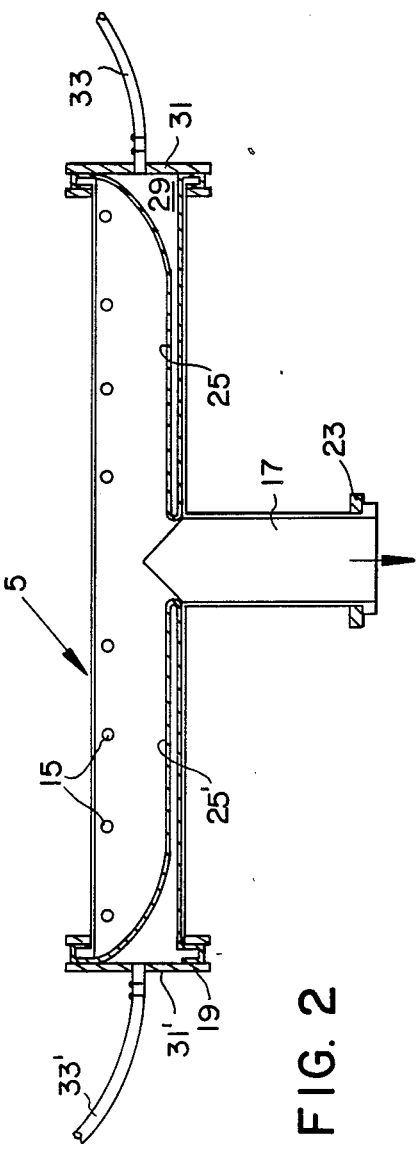

DECANTER DEVICE

BACKGROUND OF THE INVENTION (a) Field of the invention

The present invention relates to a decanter device for use to withdraw supernatant liquid from a tank containing a mixture of liquids of different densities or a mixture of a liquid and solid particles to be separated.

(b) Description of the Prior Art

Decanter devices of different structures are presently known and commonly used in the wastewater treatment industry to decant supernatant liquid from a tank or reservoir, usually called "reactor", containing a liquor to be processed, consisting of a mixture of liquids of different densities or a mixture of a liquid and solid particles.

The biological wastewater treatments which are carried out in the reactor, usually involve mechanical, biological, physical and/or chemical reactions and/or processings which result in an homogeneous mixing of the processed liquor. After sufficient reaction time, it is often necessary to separate the liquids and/or solids. Such a separation is normally done by allowing the mixture to sediment by gravity. To achieve such a sedimentation, mixing is simply interrupted for a period of time sufficient to allow for gravity separation to occur within the liquor. Then, the denser or heavier liquid or particles slowly deposit at the bottom of the reactor while the lighter or clearer liquid "moves" up to the surface, e.g. on top of the sediments, where it forms a supernatant liquid solution that can be decanted (e.g. removed) from the reactor through a pipe known as a "decanter device" leading out of the reactor and having at least one opening so located in the reactor as to enable withdrawing of the supernatant liquid.

As aforesaid, decanter devices of many kinds have been designed and are presently used to remove supernatant liquid solutions from reactors, especially from those used for carrying out the municipal and industrial wastewater treatment process known as "sequential batch reactor (SBR) treatment processes".

Considering that most applications, especially in SBR processes, require improved performances to cope with the continuous superior requirements for supernatant quality in terms of separation and suspended solids content, the decanter device to be used in the reactor tank must be very efficient and must satisfy several very specific requirements.

To better understand such requirements, it is worth reminding that during the reaction stage, the whole content of the tank is normally thoroughly mixed so that the liquor becomes homogeneous. Therefore, the solids are put in suspension and can enter the decanter device if the same simply consists of a hollow pipe or trough leading out of the tank.

During the settling stage, the solid particles that have already entered the decanter device settle within the device and thus become trapped inside. When the decanter device is operated to remove the supernatant liquid, the so-trapped solids are then flushed out of the tank, thereby greatly reducing the general performance of the process.

To avoid such a problem, three solutions have been proposed up to now.

The first solution consists in providing the decanter device with at least one gravity solids drainage opening. This opening is formed by inclined partitions merging together towards the bottom of the reactor. Such an opening can be used to withdraw the supernatant liquid as well as to drain the solids. The major inconveniences attributed to such a decanter are as follow.

First of all, keeping in mind that a high hydraulic capacity is a must to keep the productivity to its maximum, one can see that there is a real danger of disturbing the settled solids at the bottom of tank with such a decanter, where the supernatant liquid withdrawal orientation is toward from the bottom of the reactor. As a result, operation of such a device is limited, particularly if the decanter device is fixed and already submerged submerged at the desired low water level of the reactor.

Secondly, such a device does not prevent solids from penetrating. If solids are free to penetrate the decanter device, they must also be evacuated prior to operating the decanter. Some mechanical devices may succeed in doing a reasonable job but such mechanical devices must be checked regularly and maintained in proper order. A certain limitation of success is thus existing when using this type of device.

A second solution that has been proposed to solve the above mentioned problem consists in using a decanter device of the same type as above, and partially sealing the downward opening(s) of this decanter device, using an airlock to do so.

With such a design approach, a downward inclined partition opening is still used to withdraw the supernatant liquid and/or drain solids. The opening is however closed by an atmospheric air trap or lock that can be created by introduction of air in the pipe at the end of a decanting cycle or by a controlled vent line using a solenoid valve (see Canadian patent No. 1,249,228 to Mikkle Mandt).

The disadvantages of this second solution are as follow:

One again, it involves downward orientation of the supernatant liquid withdrawal.

Some solids can penetrate within of the air lock portion of the decanter and may be drained back prior to the decanting stage.

Air-trap seals are always subject to failure and may well suffer slow leaks. This may become critical particularly if not used frequently. Also, in the absence of proper heater/defrost system, ice formation in the vent line can be a serious source of problems.

The regulation opening must be in the form of a long narrow opening inside the unit. As proper head loss is critical to withdraw the liquid uniformly, a very narrow opening is used and represents a potential clogging/maintenance problem. The narrow opening is not accessible as it must be built inside the unit.

The unit must be built air tight and/watertight and thus is expensive to build. It is normally built in moulded fiberglass or stainless steel and its sealing integrity must be periodically re-checked.

A third solution that has been proposed so far to solve the above mentioned problem consists in designing the decanter device in such a manner that its inlet openings can be positioned completely out of the water so that it becomes impossible for any water/solids to penetrate during the reaction stage.

This solution is the most efficient and safe but requires serious mechanical involvements and thus quite complicated structure at the end.

OBJECT AND SUMMARY OF THE INVENTION

An object of the present invention is to provide a new decanter device which overcomes all the drawbacks of the existing devices as explained hereinabove. More particularly, the invention proposes a new decanter device which incorporates positive seal means to close its inlet openings so that no water/solids can penetrate during the reaction stage.

Another object of the invention is also to provide a new decanter device which allows efficient decantation in a reactor tank while being much less expensive to manufacture and to maintain than most of the existing devices.

In accordance with the invention, these objects are achieved with a decanter device for use to remove supernatant liquid from a tank containing a mixture of liquid of different densities or of liquid and solid particles to be separated, which device comprises:

a perforated pipe mounted inside the tank, the pipe comprising a plurality of inlets in the form of small orifices positioned along the pipe and opening into the tank, and at least one outlet leading out of the tank;

an inflatable membrane mounted inside the pipe in such a manner as to extend over the small orifices and thus sealingly close the inlets of the pipe when the membrane is inflated, and to extend away from these small apertures and away from the pipe outlet to allow supernatant liquid to flow out of the tank through this pipe when the membrane is not inflated; and means for inflating the membrane whenever desired.

In accordance with a preferred embodiment of the invention, the inflatable membrane is in the form of at least one elongated balloon extending along the pipe inside the same, and the means for inflating the membrane comprises a source of air or water under pressure operatively connected to each balloon in order to blow it up whenever desired to close the small orifices and thus seal the decanter device.

In accordance with another embodiment of the invention, the pipe extends horizontally inside said tank and the small orifices provided in the pipe are opening upwardly. Moreover, means may be provided for adjusting the height level position of the pipe inside the tank.

BRIEF DESCRIPTION OF THE DRAWINGS

The invention, the way it works and its numerous advantages will be better understood upon reading of the following non restrictive description of some preferred embodiments thereof, made with reference to the accompanying drawings in which:

FIG. 1 is a cross-sectional plan view of a decanter device according to a first embodiment of the invention;

FIG. 2 is a cross-sectional plan view of a decanter device according to a second embodiment of the invention;

GENERAL DESCRIPTION OF THE INVENTION

Figure 3:
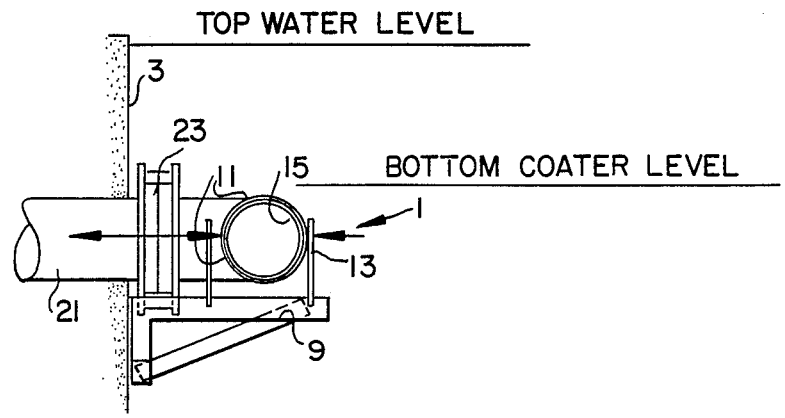
FIG. 3 is a side elevation, cross-sectional view of the right end of the devices shown in FIGS. 1 and 2.

The decanter device 1 according to the first embodiment of the invention as shown in FIGS. 1 and 3 is intended to be used to remove supernatant liquid from a tank containing a mixture of liquids of different densities or of liquid and solid particles to be separated. The device 1 comprises a perforated pipe 5 made of a standard corrosion resistant material such as polyethylene or stainless steel. The pipe 5 extends horizontally on a wall support 9 located within the tank 3 at proper level to allow supernatant liquid gravity withdrawal. As shown in FIG. 3, the pipe 5 may be mounted to the support 9 by means of steel saddles 11 and adjustable threaded studs 13.

The perforated pipe 5 comprises a plurality of inlets in the form of small calibrated orifices 15 positioned along its wall. As clearly shown, the orifices 15 are aligned and regularly spaced apart along the pipe 5. The orifices are also upwardly oriented with their axes extending from 0° to 89°, preferably from 15° to 75° and more preferably at about 45° with respect to the horizontal.

The pipe 5 also comprises at least one outlet 17 leading out of tank 3. In the embodiment shown in FIG. 1, this outlet 17 integrally extends from one opened end 19 of the pipe 5 and is connected to an effluent discharge 21 by a flange 23.

The device 1 as shown in FIGS. 1 and 3 also comprises an inflatable membrane in the form of an elongated balloon 25 made of plastic or rubber material, that extends along the pipe 5 inside the same. The balloon is sized to completely fill up the pipe when it is inflated.

This balloon 25 that can be described best as a specially designed pneumatic air chamber similar to the one used in certain vehicle tire, may be provided with two opened ends to be anchored at each end of the pipe 5. However, as is shown in FIG. 1, the balloon 25 is preferably provided with one opened end 27 only, its other end being closed or sealed depending on the decanter configuration.

The opened end of the balloon is sealingly connected to the other end 29 of the pipe which is closed by a blind flange 31. Advantageously, the balloon 25 itself may be used as a gasket as shown in FIG. 1 to seal the blind flange 31 to the end 29 of the pipe.

Inflating means are provided to blow up the balloon 25 inside the pipe 5 whenever desired. These means comprises a source of air or water under pressure connected in a flexible air or water pipe 33 and a steel or plastic hose adaptor 35 to an opening 37 provided in the blind flange 31.

As can now be understood, actuation of the inflating means causes admission of air or water under pressure in the balloon 25 and inflation of the balloon. Such an inflation can be carried out to such an extend that all the inlet orifices 15 of the pipe 5 are positively ealed. Thus, the balloon act as a diaphragm valve precluding any mixed liquid/solids from entering the decanter device and/or to discharge out of the reactor.

As long as the inflation is maintained, the liquor in the tank 3 is positively excluded from penetrating inside the pipe 5.

To operate the decanter, the pressure can simply be releasing by opening the pipe 33 to the atmosphere or connecting it to a vacuum pump.

This venting action rapidly collapses the balloon 25 inside the pipe 5 of the decanter 1, opening all its orifices 15 and thus allowing the supernatant liquid to penetrate the pipe 5 and be subsequently evacuated from the reactor via the outlet 17 and discharge 21.

It is worth mentioning that when the decanter 1 is so operated, it is always submerged in the liquid and the normal liquid submersion static pressure is sufficient to rapidly deflate (collapse) the membrane. It is also worth mentioning that the balloon 25 is anchored in such a way to the pipe 5 that it always remains in place (uniformly laid inside the decanter pipe body) while the supernatant liquid flows out, because the direction of flow is opposite from the balloon anchor point.

In accordance with a second embodiment of the invention shown in FIG. 2, the device comprises two elongated balloons 25,25' each opened at one end only. The pipe 5 is T-shaped and has two opposite ends 19 and 29 that are both closed by blind flanges 31,31'. The pipe 5 also has a central opening 17 which acts as an outlet. The opened ends of the balloons are sealingly connected to the closed ends 19,29 of the pipe 5 in the same manner as disclosed hereinabove.

Means are also provided for inflating both balloons. These means may be similar to those previously described except that they need two flexible pipes 33,33' that have to extend from the pressure source to both ends 19 and 29 of the pipe 5 to inflate both balloons simultaneously.

The following advantages are inherent of this invention:

1. It allows for upward flow withdrawal of the supernatant liquid. As a result, no hydraulic effect is created toward the bottom of the tank 3 where the heavier but easily resuspendable material or solids are settled.

2. Because only upward flow withdrawal is carried out, the decanter device 1 can be mounted at a much deeper submersion without disturbing the sludge blanket. More, the decanter device 1 can be rigidly mounted instead of being mounted on a complicated floating assembly. Such a mounting mode is simpler to fabricate, build and operate.

3. Uniform withdrawal rates all across the entire length of the decanter device 1 are achieved. Such a perfect flow regulation is very important and is positively achieved by using calibrated orifices 15 well distributed and accessible over the entire length of the pipe 5.

4. The inlet orifices are not subject to clogging. Quite large calibrated orifices 15 can be used without loosing good flow regulation due to calculated head loss through the flow passages. Continuous long, narrow openings instead of calibrated large orifices (1 to 2"$\phi$ typically) can be problematic and cause occasional clogging through solid handling, and can require maintenance in addition to being subject to promote lower performances.

5. The decanter device 1 also has a higher hydraulic capacity. As upward withdrawal is safer, higher withdrawal rate can be achieved without solids entrainment. So, larger decanter pipes 5 can be used with bigger inlet orifices 15. This allows faster withdrawal and thus increases treatment plant capacity.

6. No solid is wash-out with the supernatant liquid when the decanter device 1 is used, as solids are positively excluded from penetrating the pipe 5 at all times.

7. There is no scum or floating solids entrainment. The water level can easily be controlled so that decanting is turned off before water level reaches the level of the inlet orifice 15. Even if the inlet orifices reach the water level, the flow will be immediately interrupted as the orifices 15 will start to draw air before any appreciable quantity of scum can penetrate inside the decanter pipe 5. Then, when re-inflating the membrane or balloon 25, inner solids/liquid will be essentially expulsed from the pipe 5 by physical movement of the membrane gradually occupying all the inside space of the pipe 5.

8. The device 1 may also be used for scum withdrawal. If required, when water level reaches about 2" above the inlet orifices, the decanter can be used as a scum removal device. To achieve such a duty, the water level must be maintained at a proper valve (very close to the orifices level) so that surface currents are generated entraining the floating solids inside the pipe 5. Water level can be maintained constant by admitting water from a water source into the tank 3 (preferably treated water). Scum removal may also be achieved by keeping the inlet orifices 15 at the proper level (close to water level) by using a float mechanism or slowly turning the pipe about its axis so that the orifices 15 follow the water level down for a sufficient period of time.

9. These is no need anymore for a large effluent valve. Normally, large (8" up 30"$\phi$) effluent valves are used to control the gravity discharge of the decanter. Because the device according to the invention is essentially a "diaphragm operated valve", such large control valves or questionable air lock devices are no longer necessary.

Figure 4:
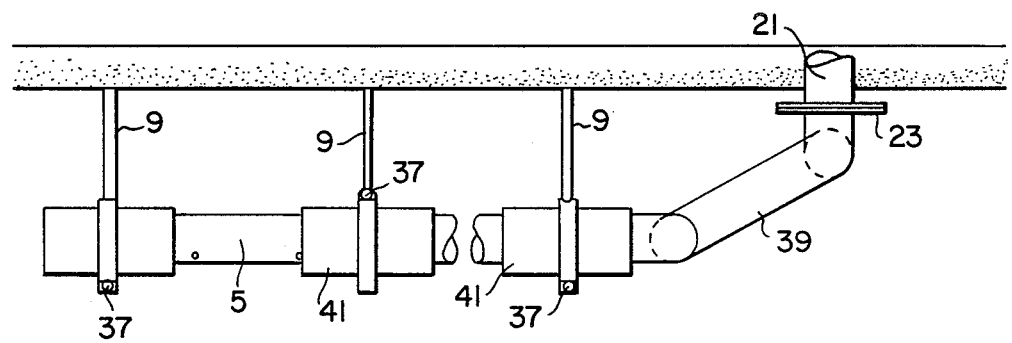
FIG. 4 is top plan view of a decanter device according to a third embodiment of the invention, which is of the floating type.
Figure 5:
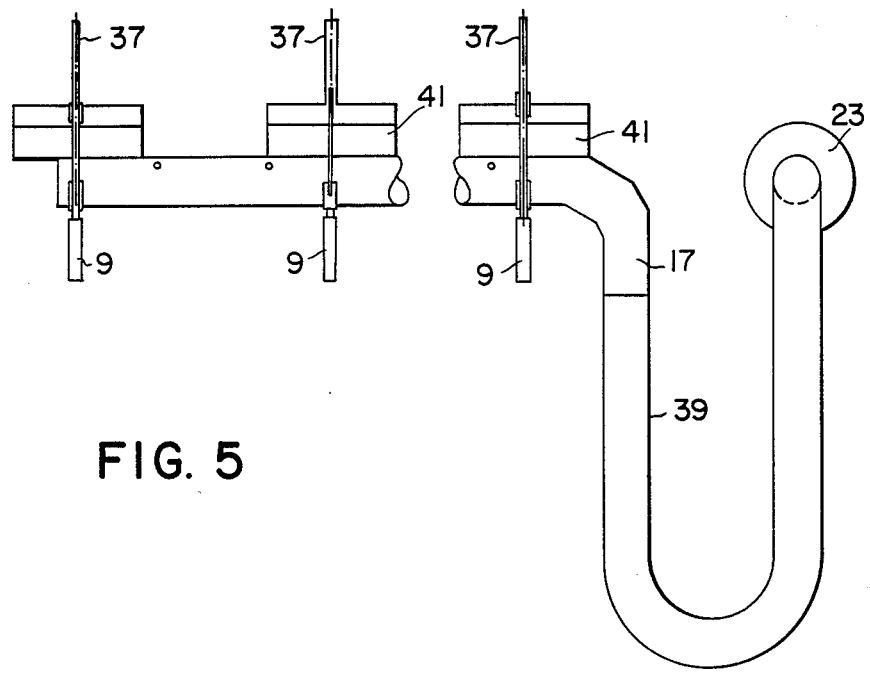
FIG. 5 is a front elevational view of the device shown in FIG. 4.
Figure 6:
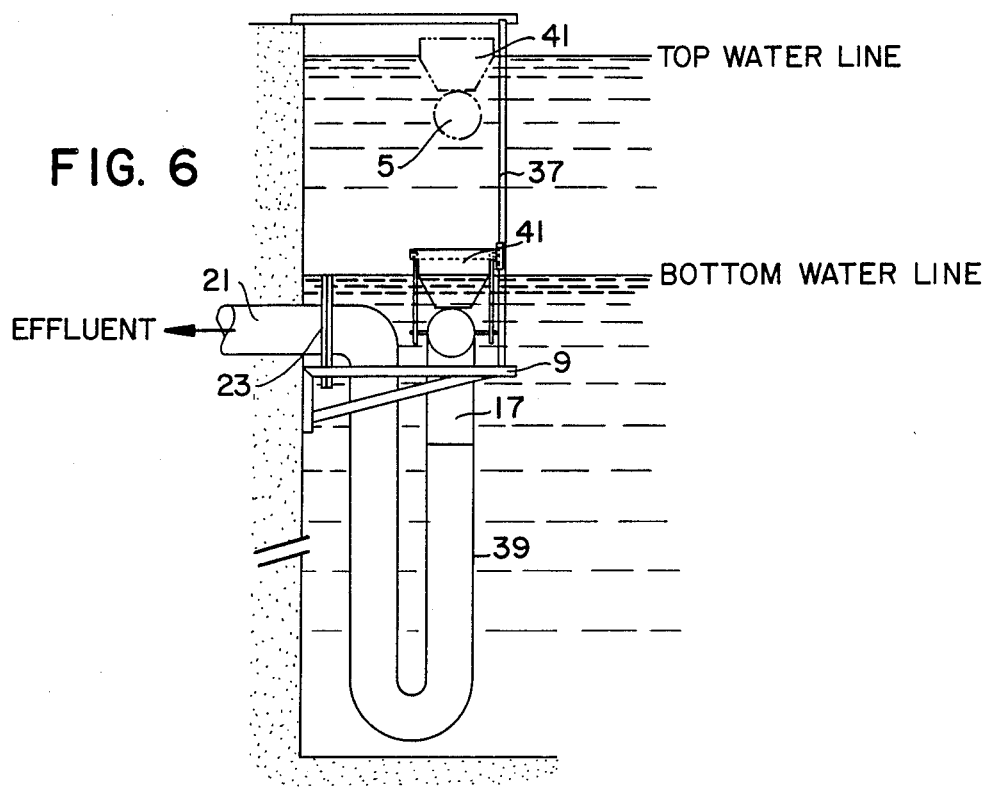
FIG. 6 is a side elevation view of the device shown in FIGS. 4 and 5.

10. The decanter device 1 can be made floating. Easy conversion of the fixed device 1 shown in FIG. 1 into a floating device can be achieved as shown in FIGS. 4 to 6. By using air as the inflating fluid, the pipe 5 can be designed to float using the air volume of the membrane only. No additional floats or mechanism are necessary. As a matter of fact, the only additional elements that are guiding rails or bars 37 extending vertically from the supports 9 to force the pipe to remain in position during its ascension and a flexible outlet conduit 39 extending between the rigid outlet 17 of the pipe and the discharge connecting flange 23 to allow the pipe to move up and down.

In such a floating mode, the position of the floating pipe 5 in the tank 3 can be adjusted in such a manner that the inlet orifices 15 drilled close to the top of the pipe 5 are brought completely out of the liquid, i.e. moved up over the level of this liquid in the reactor, hence preventing any solid or liquid from penetrating inside the pipe 5. Alternatively, the position of the floating pipe 5 can be adjusted so that the pipe 5 floats only to a certain level where the inlet orifices 15 that are maintained submerged and sealed by the balloon 25.

To achieve controlled floatation of the pipe 5, additional floats 41 as shown in FIGS. 4 to 6 can be used. Such floats 41 prevents the decanter from sinking readily under the liquor level once the balloon 25 is deflated. The floats 41 that are added allow to maintain the pipe 5 at constant submergence during the entire decantation stage of the process.

Figure 7:
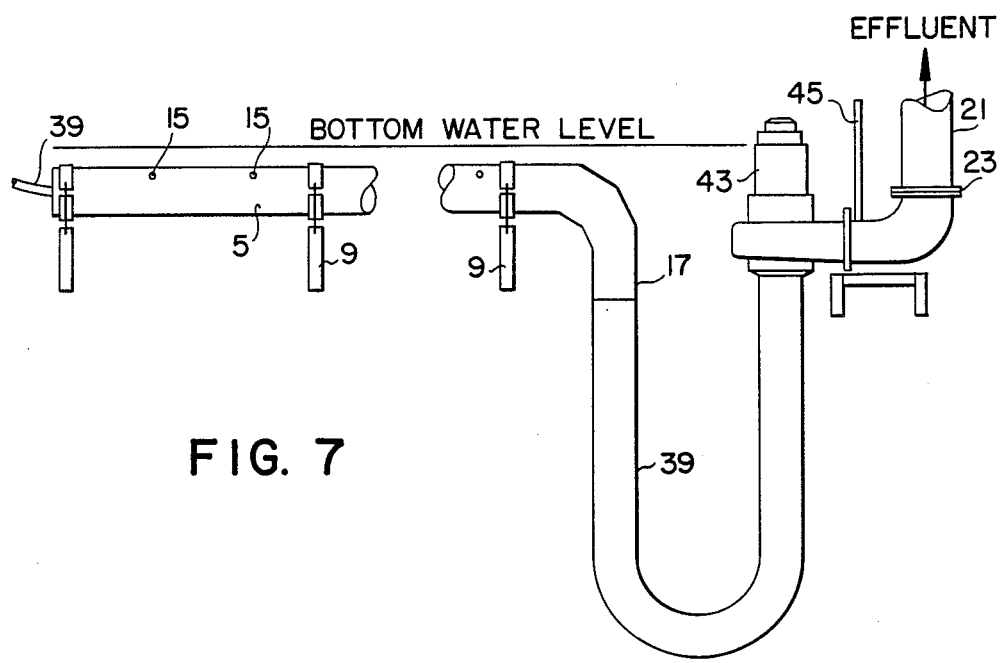
FIG. 7 is a front elevational view of a decanter device according to a fourth embodiment of the invention, which can be of the fixed or floating type and is connected to an effluent pump.

11. The decanter device 1 may incorporate a pump 43 as shown in FIG. 7. Regardless if a fixed or floating decanter device is preferred, the pump 43 may be connected to the outlet of the pipe 5 when gravity discharge is not possible. This pump 43 can be of sumbersible type or of a dry pit type.

If use is made of a submersible pump 43, a flexible section pipe 39 is recommended. The outlet of a flexible pipe 39 as disclosed hereinabove can be connected directly to the pump suction as in shown in FIG. 7 so that the pump can be readily retrieved from the water for inspection using a standard quick break-away pump discharge submerged connection and guide rail 45. This arrangement allow to conserve a perfect seal between the pump suction and the decanter pipe 5 during operation and service periods. The same flexible hose 39 of course also allows vertical movement of the device 1 if a combined floating/pumped decanter device 1 is used as is shown in FIG. 7

12. The pipe 5 used in the device according to the invention can be selected among a variety large of standard pipes available in all kind of material.

13. Operation of the decanter device 1 is very simple and can be readily understood by anyone.

14. Last of all, the device 1 according to the invention is rather inexpensive to build. Because it is made of readily available components, the device 1 can be built very inexpensively. By way of example a polyethylene pipe and a neoprene/rubber/ plastic membrane can be used to manufacture it. The pipe can also be replaced by another body of the same type, such as a through or conduit of any shape.

The decanter device 1 according to the invention can be used wherever supernatant liquid must be removed from a tank as part of a process. Main applications can be enumerated as into:

Oil separator tanks in the refiners industries;

Chemical solution tanks in the chemical industries;

Water and liquor tanks in the drinking and food industries;

Water and other liquid tanks in the chemical/physical treatment industries; and

Water tank in the biological/physical treatment industries.

One of the preferred applications is certainly the separation of solids from a mixed biological liquor as intensively used to treat municipal and industrial wastewater. More particularly, the device according to the invention is capable of being applied into biological digesters where adjustment in the concentration of biological solids is achieved by decanting the supernatant water and subsequently adding more mixed liquor.

Another preferred application is in the biological waste treatment process known as Sequential Batch Reactor (SBR) process. In this process, the wastewater is treated as a standard aerobic activated sludge but using sequential batch volumes to do so. Usually, several reactor tanks must be used if wastewater is to be handled in a continuous way, because the treatment process is occurring in a closed reactor e.g. with intermittent discharges only once the biological treatment has been achieved. In such a SBR process, large quantities of clear, treated water must be discharged quickly and efficiently out of each reactor tank at the end of each batch treatment or cycle, thereby requiring a specially designed decanter device.

As can be understood, the invention described hereinabove is particularly well designed to provide the best possible performance for such application into SBR.

The embodiments of the invention in which an exclusive property or privilege is claimed are defined as follows:

1. A decanter device for use to withdraw supernatant liquid from a tank containing a mixture of liquids of different densities or liquid and solid particles to be separated, said device comprises:

a perforated pipe mounted inside the tank, said pipe comprising a plurality of inlets in the form of small orifices positioned along said pipe and opening into the tank, and at least one outlet leading out of said tank;

an inflatable membrane mounted inside the pipe in such a manner as to extend over said small orifices and sealingly close the inlets of said pipe when said membrane is inflated, and to extend away from said small orifices and away from said at least one outlet to allow supernatant liquid to flow out of the tank through said this pipe when the membrane is not inflated; and means for inflating the membrane whenever desired.

2. A decanter device as claimed in claim 1, wherein said inflatable membrane is in the form of at least one elongated balloon extending along the pipe inside the same, and wherein said means for inflating said membrane comprises a source of air or water under pressure operatively connected to said at least one balloon in order to blow it up whenever desired, to close said small orifices.

3. A decanter device as claimed in claim 2, wherein said pipe extends horizontally within said tank, and wherein said small orifices provided in said pipe -are upwardly oriented.

4. A decanter device as claimed in claim 2, wherein:
said device comprises one elongated balloon exclusively;
said elongated balloon is opened at one end only;
said opened end of the balloon is sealingly
said pipe has another, opened end which acts as said outlet; and
said means for inflating said membrane further comprise an air or water pipe connecting said air or water source to an opening provided in said one closed end of said pipe.

5. A decanter device as claimed in claim 4, wherein:
said pipe extends horizontally within said tank;
said other end of said pipe is sealingly connected to a flexible outlet extension leading out of said tank; and
said decanter device further comprises means for adjusting in height the position of said pipe inside said tank.

6. A decanter device as claimed in claim 2, wherein:
said device comprises two elongated balloons;
each of said balloons is opened at one end only;
said pipe has two opposite closed ends and a central opening acting as said outlet;
said opened ends of said balloons are sealingly connected to said closed ends of said pipe, respectively; and
said means for inflating said membrane further comprise air or water pipes connecting said air or water source to openings provided in both of said closed ends of said pipe.

7. A decanter device as claimed in claim 6, wherein:
said pipe extends horizontally inside said tank;
said outlet opening of said pipe is sealingly connected to a flexible outlet extension leading out of said tank; and
said decanter device further comprises means for adjusting in height the position of said pipe inside said tank.

* * * * *